(12) United States Patent
Blank

(10) Patent No.: US 12,064,254 B2
(45) Date of Patent: Aug. 20, 2024

(54) HAIR CONDITION-DETERMINING DEVICE, HAIR CONDITION-DETERMINING SYSTEM, AND METHOD FOR DETERMINING A HAIR CONDITION

(71) Applicant: Henkel AG & Co. KGaA, Duesseldorf (DE)

(72) Inventor: Philippe Blank, Kleve (DE)

(73) Assignee: HENKEL AG & CO. KGAA, Duesseldorf (DE)

(*) Notice: Subject to any disclaimer, the term of this patent is extended or adjusted under 35 U.S.C. 154(b) by 1296 days.

(21) Appl. No.: 16/609,365

(22) PCT Filed: May 29, 2018

(86) PCT No.: PCT/EP2018/063984
§ 371 (c)(1),
(2) Date: Oct. 29, 2019

(87) PCT Pub. No.: WO2018/219892
PCT Pub. Date: Dec. 6, 2018

(65) Prior Publication Data
US 2020/0196936 A1 Jun. 25, 2020

(30) Foreign Application Priority Data
May 31, 2017 (DE) ...................... 10 2017 209 225.4

(51) Int. Cl.
*A61B 5/00* (2006.01)
*A45D 24/10* (2006.01)
(Continued)

(52) U.S. Cl.
CPC .............. *A61B 5/448* (2013.01); *A45D 24/10* (2013.01); *A45D 44/005* (2013.01); *A46B 9/023* (2013.01);
(Continued)

(58) Field of Classification Search
CPC ..... A61B 5/448; A61B 5/0013; A61B 5/0071; A61B 5/0082; A61B 5/486; A61B 5/6887;
(Continued)

(56) References Cited

U.S. PATENT DOCUMENTS

2008/0218732 A1* 9/2008 Mil'shtein ........... G01N 21/359
356/51
2009/0036800 A1* 2/2009 Rabin .................. A61B 5/1072
600/587
(Continued)

FOREIGN PATENT DOCUMENTS

DE 19506677 A1 8/1996
FR 3000877 A1 * 7/2014 ......... A46B 15/0006
(Continued)

OTHER PUBLICATIONS

EPO, International Search Report issued in International Application No. PCT/EP2018/063984, dated Jul. 19, 2018.

*Primary Examiner* — Bo Joseph Peng
(74) *Attorney, Agent, or Firm* — Lorenz & Kopf, LLP

(57) ABSTRACT

A hair condition-determining device can have a device body having at least one first region and one second region, wherein the first region and the second region are designed in such a way that the hair of the user can be moved between the first region and the second region, at least one optional light source arranged in or on the device body for illuminating the hair of the user, at least one optical sensor arranged in or on the device body for sensing light that has been emitted by the light source and has interacted with the hair and/or ambient light that has interacted with the hair, and an electronic circuit device arranged in or on the device body, wherein the electronic circuit device is coupled to the optical sensor in order to receive the detected light.

14 Claims, 9 Drawing Sheets

(51) Int. Cl.
*A45D 44/00* (2006.01)
*A46B 9/02* (2006.01)
*A46B 15/00* (2006.01)
*G09B 19/00* (2006.01)

(52) U.S. Cl.
CPC ...... *A46B 15/0002* (2013.01); *A46B 15/0034* (2013.01); *A61B 5/0013* (2013.01); *A61B 5/0071* (2013.01); *A61B 5/0082* (2013.01); *A61B 5/486* (2013.01); *A61B 5/6887* (2013.01); *A61B 5/742* (2013.01); *G09B 19/00* (2013.01); *A45D 2044/007* (2013.01); *A46B 2200/104* (2013.01); *A61B 2562/0204* (2013.01)

(58) Field of Classification Search
CPC ............ A61B 5/742; A61B 2562/0204; A61B 2503/12; A45D 24/10; A45D 44/005; A45D 2044/007; A46B 9/023; A46B 15/0002; A46B 15/0034; A46B 2200/104; G09B 19/00; G16H 40/63; G01N 21/359; G01N 21/645
See application file for complete search history.

(56) References Cited

U.S. PATENT DOCUMENTS

2011/0155161 A1\* 6/2011 Samain ................ A45D 44/005
                                                      401/137
2012/0320191 A1  12/2012 Meschkat et al.
2015/0342515 A1  12/2015 Hutchings et al.

FOREIGN PATENT DOCUMENTS

WO        0224071 A2    3/2002
WO     2017032636 A1    3/2017

\* cited by examiner

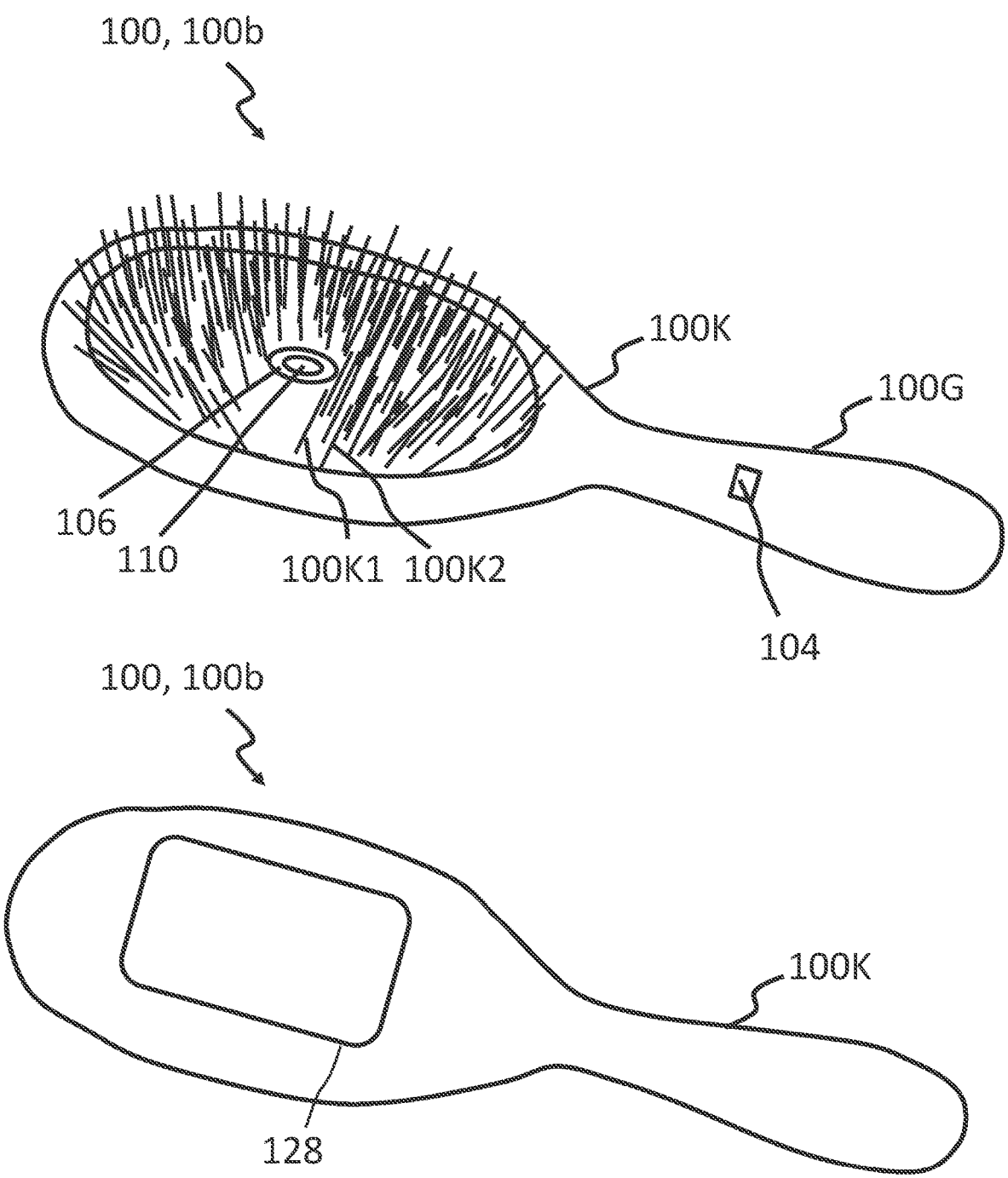

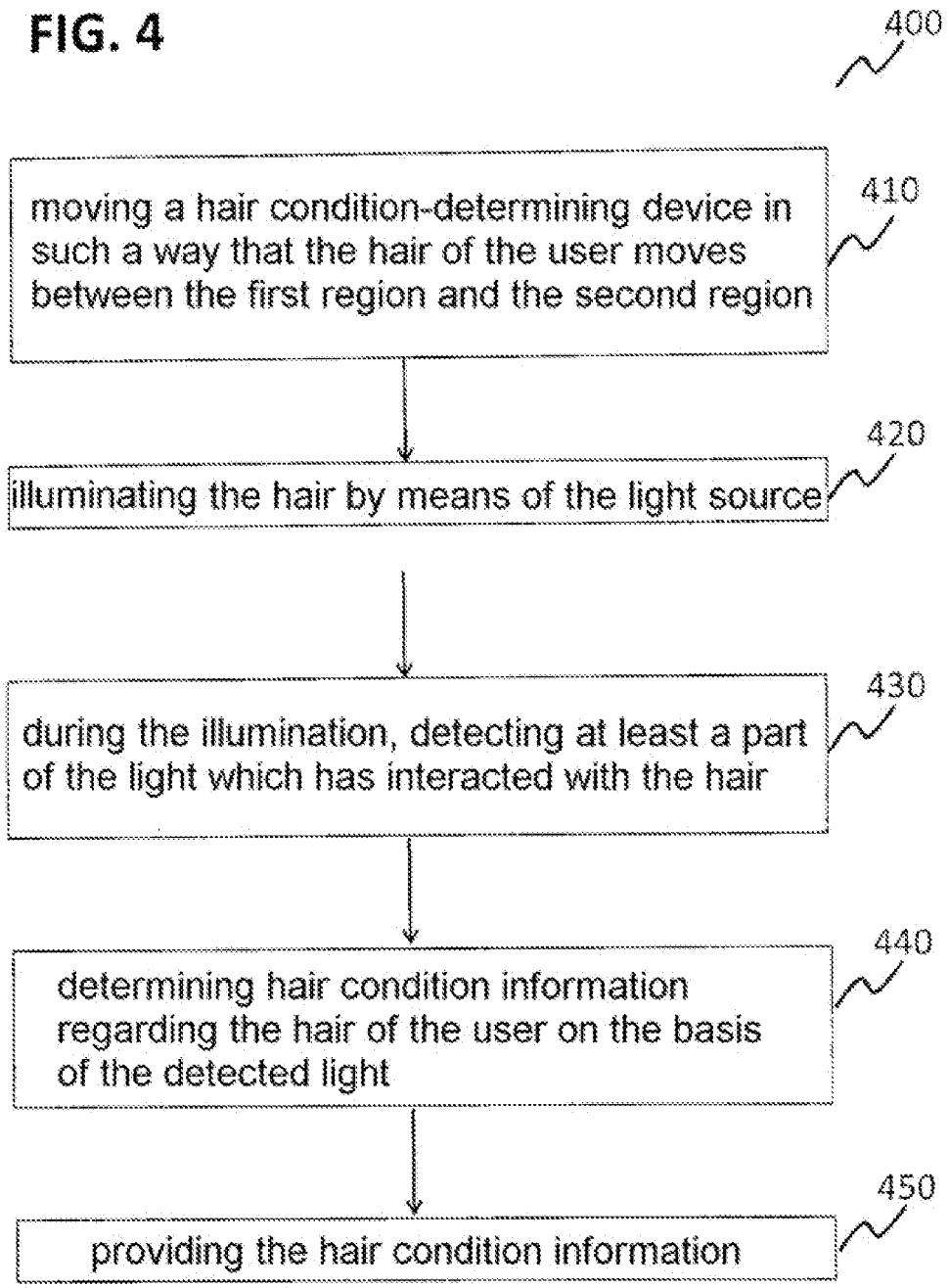

HAIR CONDITION-DETERMINING DEVICE, HAIR CONDITION-DETERMINING SYSTEM, AND METHOD FOR DETERMINING A HAIR CONDITION

CROSS-REFERENCE TO RELATED APPLICATION

This application is a U.S. National-Stage entry under 35 U.S.C. § 371 based on International Application No. PCT/EP2018/063984, filed May 29, 2018, which was published under PCT Article 21(2) and which claims priority to German Application No. 10 2017 209 225.4, filed May 31, 2017, which are each hereby incorporated in their entirety by reference.

TECHNICAL FIELD

The present disclosure relates to a hair condition-determining device, hair condition-determining system, and a method for determining a hair condition.

BACKGROUND

In many areas of daily life there has been a trend, for some time now, towards personalised programs which can respond selectively to individual requirements and needs, for example in the nutrition or health sector, but also in the field of personalised cosmetics. These can allow a user to selectively find cosmetic products and/or obtain care recommendations, which are matched to the individual needs of the user's hair and thus enable a particularly high efficacy.

When treating hair with cosmetic products an effect of the product, for example the intensity of a colouration, the efficacy of a care product, or a hair shaping effect of a perm, may be heavily dependent on the hair condition, in particular the degree of damage of the hair.

Thus, it may be of great significance to determine the level of damage of the hair, and this may constitute an important parameter for the user for the (objective) assessment of his/her hair health.

Hair damage may occur by natural or man-made processes. The most important type of damage may be oxidative damage in this context.

The natural processes may include, for example, a combined (for example simultaneous) effect of UV light and oxygen ($O_2$) on the hair.

The man-made processes in this context may include, for example, the use of hair dyes (also referred to as colourants, which in the case of the present application also includes bleaching), and/or a styling or shaping of the hair (for example the creation of a perm).

Besides desired, cosmetic effects, such as a lightening of the hair, considerable damage to the hair may also occur, for example if oxidisers are used.

In the case of damaged hair for example a cysteic acid content may be increased due to the oxidation of the amino acids cystine and cysteine, which are encountered very frequently in hair, to form cysteic acid.

The oxidation of the cystine/cysteine to form cysteic acid may destroy the mechanical stability of the hair and, in the case of multiple applications, may even lead to a complete hair breakage. Properties of the hair that before were already perceptible on a macroscopic scale, for example feelable, such as a surface condition, for example a surface roughness, may be negatively influenced. Damaged hair for example may have a higher surface roughness than undamaged hair.

BRIEF SUMMARY

This disclosure provides a hair condition-determining device for providing information regarding a hair condition of hair of a user, the device having:
a device body having at least one first region and one second region, which are formed such that the hair of the user can be moved between the first region and the second region;
at least one optional light source, arranged in or on the device body, for illuminating the hair of the user;
at least one optical sensor, arranged in or on the device body, for detecting light which has been irradiated by the light source and has interacted with the hair, and/or ambient light which has interacted with the hair; and
electronic circuit device arranged in or on the device body,
wherein the electronic circuit device is coupled to the optical sensor in order to receive a signal generated by employing the detected light, and
wherein the electronic circuit device is designed to determine information regarding the hair condition of the user on the basis of the received signal and to provide the information to the user.

This disclosure also provides a hair condition-determining system having:
the aforementioned hair condition-determining device
a display device,
wherein the at least one hair condition-determining device is designed to transmit the hair condition information to the display device by employing the data exchange device.

This disclosure also provides a method for providing hair condition information regarding hair of a user, having the steps:
arranging a hair condition-determining device according to claim 1 in such a way that the hair of the user faces a light entry region of the hair condition-determining device;
optionally illuminating the hair by employing the light source;
during the illumination as applicable, detecting at least a part of the light which has interacted with the hair and/or detecting ambient light which has interacted with the hair;
determining hair condition information regarding the hair of the user on the basis of the detected light; and
providing the hair condition information.

BRIEF DESCRIPTION OF THE DRAWINGS

The present disclosure will hereinafter be described in conjunction with the following drawing figures, wherein like numerals denote like elements, and:

FIGS. 1A and 1B each show a schematic depiction of a hair condition-determining device according to various exemplary embodiments;

FIG. 4 shows a flow chart illustrating a method for determining a hair condition in accordance with various exemplary embodiments.

DETAILED DESCRIPTION

Figure 1A:
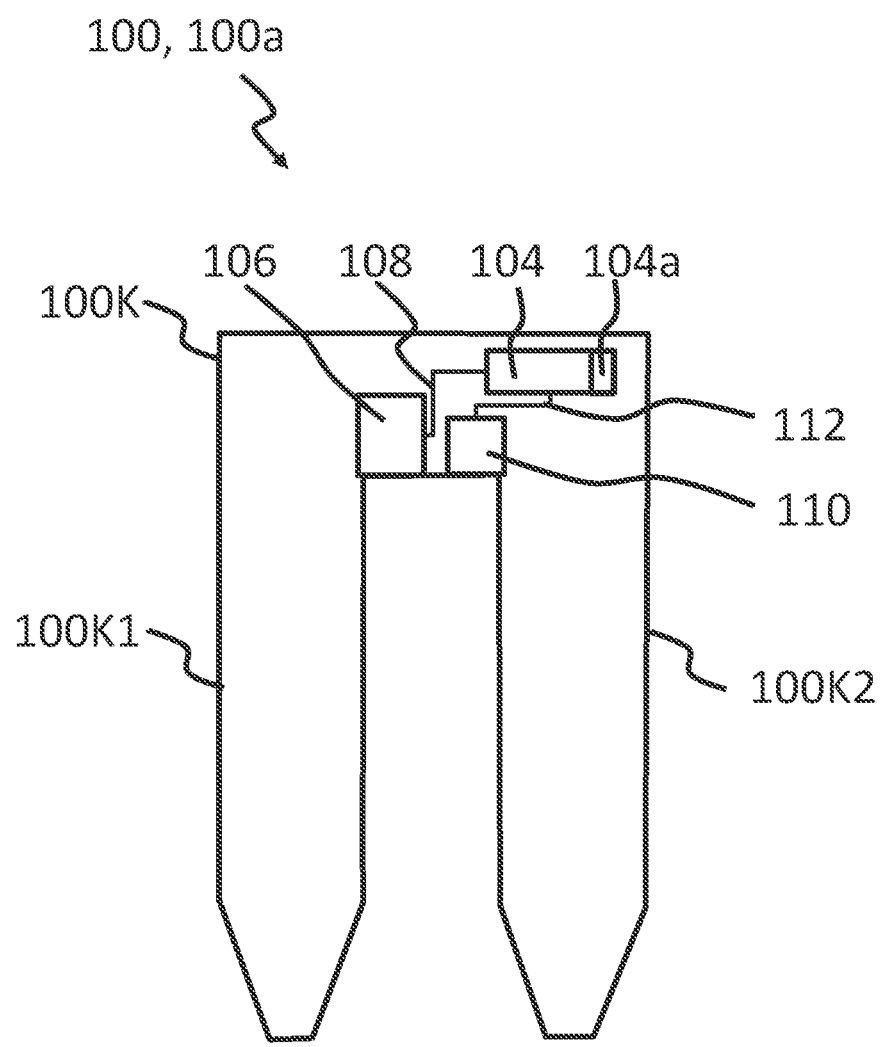

The following detailed description is merely exemplary in nature and is not intended to limit the disclosure or the application and uses of the subject matter as described herein. Furthermore, there is no intention to be bound by any theory presented in the preceding background or the following detailed description.

Reference is made in the following detailed description to the accompanying drawings, which form part of the present application and in which specific embodiments in which the present disclosure can be carried out are shown by way of illustration. It goes without saying that other embodiments can be used and structural or logical changes can be made without departing from the scope of protection of the present disclosure. It goes without saying that the various exemplary embodiments described herein can be combined with one another unless specifically stated otherwise. The following detailed description therefore is not to be interpreted as limiting, and the scope of protection of the present disclosure is defined by the accompanying claims.

Human hair is formed from proteins, lipids, water, trace elements and pigments. The fibre protein keratin is the main constituent of hair. The lipids that are present in human hair are either free or covalently bonded. Melanins are reddish, brown or black pigments, which provide the colour of the hair.

Results of cosmetic treatments may be dependent on further properties of the treated hair, for example (in particular in the case of colouration) on a hair colour, on a hair structure (in particular in the case of a styling process, for example a perm, a straightening, etc.), on a moisture content (in the case of a care product), etc.

A hair condition-determining device which makes it possible to determine the condition of the hair of a user by employing an optical sensor is provided in various embodiments. In various exemplary embodiments the hair condition can be determined whilst the hair is being brushed or combed, i.e. the hair condition-determining device can be provided in the form of a comb or brush. In various exemplary embodiments a recommendation can be provided on the basis of the determined hair condition, for example a recommendation regarding a cosmetic care treatment product and/or a hair treatment recommendation.

An optical sensor shall be understood herein to mean a sensor which, by employing optical elements, conducts light in the broader sense (UV light, visible light (also referred to as the EIS for short), near-infrared light (NIR) and/or infrared light (IR)) and detects it by employing a detector (for example an electronic detector, for example for visible light, for NIR light and/or IR light, a photometer, or the like).

Reference may be made herein to "the sensors", for example with regard to a data transfer between the sensors and the data processing device, an arrangement of the sensors, etc. This shall be understood in the sense that the sensors may comprise a totality of sensors and/or sensor circuits arranged in or on the device body, for example a totality of optical sensor(s) (for example spectrometer, camera, microscope), microphone(s), speed sensor circuit, etc., or, if evident from the context, a part of the aforesaid sensors and/or sensor circuits.

In order to directly or indirectly determine the hair condition and optionally in order to directly or indirectly determine the recommendation (for example of the hair treatment product and/or the hair treatment recommendation), the device or the system in various exemplary embodiments may have a data processing device.

The hair condition may comprise a level of hair damage and/or a hair status.

In various exemplary embodiments the hair damage may be oxidative hair damage, surface damage, or mechanical hair damage.

The hair status may include in particular a hair colour, a content of a hair constituent, a hair thickness, a curliness of hair and/or a proportion of grey hairs.

The hair constituent may comprise in particular water, melanins, lipids, amino acids and mixtures thereof. A preferred hair constituent of which the content is ascertained in order to determine a hair status is water.

Human hair contains not only the 20 canonical amino acids glycine, alanine, valine, isoleucine, leucine, phenylalanine, tyrosine, lysine, arginine, histidine, aspartic acid, glutamic acid, threonine, serine, glutamine, asparagine, methionine, cysteine, proline and tryptophan, but also the amino acids cystine, ornithine and citrulline. Accordingly, it is preferred that the hair constituent of which the content is ascertained is an amino acid selected from the group including glycine, alanine, valine, isoleucine, leucine, phenylalanine, tyrosine, lysine, arginine, histidine, aspartic acid, glutamic acid, threonine, serine, glutamine, asparagine, methionine, cysteine, proline, tryptophan, cystine, ornithine, citrulline and mixtures thereof.

In various exemplary embodiments at least one hair parameter can be determined by user or a hairdresser with the aid of a comb or a brush, which is provided at least with an optical sensor. This means that at least one hair parameter can be determined during a combing/hairstyling process that takes place anyway within the scope of a haircare regime.

In various exemplary embodiments the optical sensor may be, for example, a near-infrared sensor (NIR sensor), for example an NIR spectrometer or an NIR camera, which may be designed to determine hair damage and/or the hair condition.

In various exemplary embodiments the optical sensor may be, for example, a sensor for visible light, for example a spectrometer or a camera for a spectral range of the visible light, in particular in a range in which fluorescent light is emitted by the hair. Here, the optical sensor may be designed to determine hair damage and/or the hair condition.

The optical sensor for visible light or a further sensor for visible light, for example a spectrometer or a colour camera, may be designed in various exemplary embodiments to determine a starting hair colour of the user. In the case in which the camera (or an additional camera) is provided, this may also be used to determine a further hair status, such as a hair density and/or a hair thickness.

In various exemplary embodiments a further sensor can be provided, for example a (contact) microphone for determining a surface roughness of the hair, which constitutes a measure for surface damage of the hair.

The optical sensor for determining the hair damage or the hair status (for example an NIR sensor) can be provided in a basic embodiment of the hair condition-determining device, whereas a premium embodiment may include at least one further sensor, for example the (contact) microphone, which can be arranged in/on teeth of the comb or the brush, or a further optical sensor. The optical sensor and the further optical sensor may each be arranged at different positions on or in the device body.

In various exemplary embodiments a combination of a number of the above-mentioned sensors may make it possible to obtain a more comprehensive picture of the hair condition. A sensing of two or more hair conditions may be understood to mean a two-dimensional or multi-dimensional measurement, by employing which an analysis result regarding the hair condition can be improved.

In various exemplary embodiments an input device can be used in order to input a desired result, for example a desired hair colour, a desired state of nourishment, a desired styling (for example curly with graduated curliness, or the like). In addition, the input device can be used in order to provide the hair condition-determining device with further information which can be taken into consideration optionally when determining the recommendation, for example whether a product should possibly be waterproof, should contain UV protection, age and/or gender of the user (for example for a case in which a care product is provided with a fragrance), etc.

In various exemplary embodiments the hair condition-determining device, when determining the recommendation, for example of the hair treatment agent, may take into consideration the desired result in such a way that the recommended product and/or the recommended hair treatment is suitable to provide the desired result on the hair of the user.

In a case in which the hair condition-determining device comprises the microphone, the microphone can also be used as an input microphone in various exemplary embodiments.

In various exemplary embodiments another conventional input device, for example buttons, a touch-sensitive screen, etc., can be provided alternatively or additionally as input device on the hair condition-determining device.

The hair condition-determining device in various exemplary embodiments can have an output device for outputting the hair condition information and/or the recommendation, for example a loudspeaker and/or display.

In various exemplary embodiments the hair condition-determining device can be part of a hair condition-determining system which can also comprise at least one display device, which can be used as an output device for the hair condition information and/or the recommendation.

In various exemplary embodiments, for example if the display device is a smartphone, tablet, a smart mirror, or the like, the display device can also be used as an input device and/or as an external data processing device.

In various exemplary embodiments the styling element or feature may comprise a hair wax or gel, straightener, hairspray, a hair mousse, or the like.

In various exemplary embodiments, data and/or experience values from (other) users, who may have a similar hair condition (for example a similar degree of damage and/or a similar hair status) and possibly a similar profile (age, gender, lifestyle habits, hair type, ethnicity, etc.), can be taken into consideration when determining the recommendation. A broad data and/or experience record can be used here in order to optimise the result. The system may possibly be configured as a learning system.

In various exemplary embodiments the hair condition-determining device may be designed to transmit a current hair damage condition of a user, which for example may have been determined by employing the NIR sensor, from the hair condition-determining device (for example a so-called "smart comb") to a hair treatment agent mixing device, which can determine an individual hair treatment agent composition and can provide a corresponding hair treatment agent to the user.

In various exemplary embodiments a standardised and objective assessment of the treatment result can be made possible by employing the hair condition-determining device. For this purpose, the hair condition of the user once the recommendation has been followed, for example once the recommended product has been applied and/or once the recommended treatment has been carried out, can be determined by employing the optical sensor and possibly further sensors contained in the brush or the comb.

Continuous, possibly frequent, measurements of reliable hair damage values made possible as a result may allow the user to track his/her state of hair health over time and to increase his/her confidence in the success of the treatment.

A design of the device body in the form of a comb or brush which is intended to move the hair between comb teeth or brush bristles, this being performed typically in such a way that the hair touches a carrier region carrying the teeth or bristles, makes it possible to arrange the optical sensor in the carrier region, which can mean that the hair is arranged reliably at a fixed predetermined distance from the sensor without having to follow complex instructions and/or without having to provide a spacer, thus improving the consistency and reliability of the measurement results.

In various exemplary embodiments the hair condition-determining device can be designed such that it is possible to determine the degree of (oxidative) hair damage in a precise manner by employing the optical sensor by ascertaining the content of cysteic acid. The optical sensor can be designed to take one or more recordings in a fluorescence range and/or in a near-infrared range (NIR range).

The fluorescence range in various exemplary embodiments may be a wavelength range in which damaged hair emits inherent fluorescence and/or a wavelength range in which fluorescence dyes, which are adsorbed to a greater extent by damaged hair than by undamaged hair, emit fluorescent light.

The near-infrared range in various exemplary embodiments may be a wavelength range in which (damaged) hair has absorption structures, for example in which water or cysteic acid absorbs light. In the case of near-infrared spectroscopy, the detection takes place in the near infrared (about 780 to about 2,500 nm or approximately 12,800 to about 4,000 $cm^{-1}$). Hereinafter, the term "near-infrared" (NIR) will be used for light with a wave number in a range of from about 12,800 to about 4,000 $cm^{-1}$, and the term "infrared" (IR) will be used for light with a wave number in a range of from about 3,999 to about 400 $cm^{-1}$.

Undamaged hair may typically have a cysteic acid content in a range of from approximately 0.5% to approximately 1% (by weight). If there is damage present, for example as a result of repeated extreme bleaching and/or other damage mechanisms, the cysteic acid content may rise to more than about 15% (by weight).

In various exemplary embodiments this property is used to quantify the degree of damage of the hair in the form of a content of cysteic acid.

In various exemplary embodiments damaged hair may have an inherent fluorescence, which is used to determine the degree of damage by detecting the fluorescence intensity of the hair.

In various exemplary embodiments the hair can be wetted with a fluorescence dye solution, which is better absorbed by damaged hair than by undamaged hair, wherein the fluorescence dye solution can comprise rhodamine B, coumarin and/or fluoroscein.

In various exemplary embodiments the hair can be illuminated by employing the light source by UV light (for example by light in a wavelength range of from approximately 315 nm to approximately 380 nm) in order to determine the fluorescence intensity of the hair. For this purpose, the sensor device can be provided with a UV light source. The UV light source may be a UV LED or another suitable light source which is small enough to be accommodated in the body of a comb or brush.

During the illumination, fluorescent light which is emitted by the hair can be recorded. The fluorescence intensity can be determined on the basis of the recorded light. The degree of damage of the hair can then be determined taking into account the fluorescence intensity of the hair.

Accordingly, the optical sensor can be capable of receiving at least within the fluorescence wavelength range. The optical sensor for example may comprise or be a camera, a photometer, a colorimeter and/or spectrometer. In various exemplary embodiments a filter can be arranged between the hair and the optical sensor.

Thanks to the technological advances in recent years, optical sensors (for the visible wavelength range or for the NIR or IR range) are now available which are small enough to be accommodated in the body of a brush or the like.

In various exemplary embodiments, for example in a case in which the optical sensor, for example a detector of the optical sensor and/or optical components such as a dispersing element of a spectrometer or the like, requires more space than is available in the vicinity of the hair (for example in a tooth region of a comb), it is possible for at least one light-guiding device to be provided. Here, the component requiring space (for example the light source and/or the detector) can be arranged at a point of the hair condition-determining device which has more space available, for example in a comb or brush handle, and the at least one light-guiding device can be designed such that it guides light (for example the light for illuminating the hair or the light which has interacted with the hair) between the component and an entry or exit point of the light on the device body. It is possible to use, as light-guiding device, conventional structures known for this purpose, for example light-guiding fibres, light-guiding channels, mirrors and/or other optical elements, etc., wherein it must be ensured that a light-permeable material, if used, is light-permeable for the particular wavelength range that is to be guided, for example in the case of NIR light with the NIR wavelength range up to approximately 2.5 µm.

In various exemplary embodiments the near-infrared (NIR) spectrum and/or an infrared (IR) spectrum can be obtained, for example by employing ATR (near-)infrared spectroscopy (ATR=attenuated total reflection). By use of mathematical models, a mathematical model can be created by measuring calibration hair samples which have a cysteic acid content determined on the basis of a known analytical method.

With analysis of an NIR or IR spectrum recorded on the hair of the consumer, or at least part thereof, the model in various exemplary embodiments can allow a calculation of the content of cysteic acid, and thus of the hair damage. An analysis of at least part of the spectrum and an application of the model can be realised here by employing the data processing device, for example (using suitable apps) by employing known smartphones, tablets, smart mirrors, or the like.

The light source in various exemplary embodiments can be an NIR light source and/or an IR light source for illuminating the hair using NIR or IR light.

In accordance with various exemplary embodiments, the degree of damage of hair can be determined with use of the near-infrared range, i.e. by irradiating the hair with a near-infrared light and by spectral analysis of at least part of the NIR light, once this has interacted with the hair, or with use of the infrared range, i.e. by irradiating the hair with infrared light and by spectral analysis of at least part of the IR light, once this has interacted with the hair, or with use of both the near-infrared range and infrared range, i.e. by irradiating the hair with near-infrared and infrared light and by spectral analysis of at least part of the NIR light and at least part of the IR light, once this has interacted with the hair.

In various exemplary embodiments a measured near-infrared (NIR) range can have wave numbers of from approximately 12,500 $cm^{-1}$ to approximately 4,000 $cm^{-1}$, for example of from approximately 5,022 $cm^{-1}$ to approximately 4,020 $cm^{-1}$. This wavelength range can have, amongst other things, characteristic harmonic and combination vibrations of, for example, CH, OH and NH groups.

In various exemplary embodiments the least one part of the near-infrared and/or infrared light can have a (infrared) wave number range of from approximately 1100 $cm^{-1}$ to approximately 1000 $cm^{-1}$, for example around approximately 1040 $cm^{-1}$. Amongst other things, the relevant absorption bands of the component to be analysed (cysteic acid) can be found here.

In various exemplary embodiments, a calibration model can be created on the basis of results of a quantitative computer-aided evaluation (also referred to as chemometric analysis) for a plurality of calibration hair samples in combination with values for a cysteic acid content of each calibration hair sample obtained by employing an independent method, for example by employing high-pressure liquid chromatography, for said same calibration hair samples.

If the calibration model is present, in various exemplary embodiments the concentration of the cysteic acid (as a measure for hair damage) for the hair that is to be measured can be calculated very easily from the spectra in comparison with the calibration spectra on the basis of the recorded (N)IR spectrum.

In various exemplary embodiments suitable mathematical models based on predictive analytics can be used for the quantification of the cysteic acid content (for example by employing fluorescence analysis and/or by employing (N)IR spectroscopy) or the degree of damage (for example by employing interference reflection microscopy and/or by employing acoustic analysis).

In various exemplary embodiments an easily implemented method is provided, which enables a precise determination of a degree of oxidative damage of hair with the aid of fluorescence detection and/or by detection of absorption and methods based on predictive analytics.

In various exemplary embodiments a portable data processing device, also referred to as a mobile data processing device, can be used to provide the determined hair condition or the recommendation. For example, a smartphone, an iPad, a tablet, or laptop can be used as portable data processing device.

In various exemplary embodiments a method can be provided which makes it possible to provide information regarding the hair condition of a user, and optionally a recommendation on that basis, by employing simple image-analysis methods, which for example are performed with use of a simple device (for example a UV-LED, a white light, NIR and/or IR lighting device, a filter, a portable NIR sensor, a (NIR and/or VIS) spectrometer arranged in or on the device body of the determination device, possibly in conjunction with a mobile data processing device (for example a smartphone) and possibly a method based on predictive analytics.

In various exemplary embodiments the intensity of the absorption of the (N)IR light by the cysteic acid or the intensity of fluorescent light can be easily detected with the aid of image-analysis methods under standardised conditions. By application of mathematical models from the field of predictive analytics, by measuring standard hair samples, which have a cysteic acid content determined on the basis of known complex methods, a mathematical model can be created which makes it possible to calculate the content of cysteic acid, and thus the level of hair damage, for the hair of the consumer on the basis of the recorded (N)IR absorption or the recorded fluorescent light and the fluorescence intensity determined therefrom. The image analysis can be performed here for example (using suitable apps) by employing known smartphones, tablets, or the like.

In various exemplary embodiments the use of the mathematical models from the field of predictive analytics (such as tree ensembles, neural networks or support vector machines) allows a much more precise calculation of the damage (which forms a dependent variable in the models) than would be possible with simple models, for example a simple linear regression. The methods can use multiple input variables in parallel and can also illustrate non-linear relationships. In various exemplary embodiments these models for example enable the inclusion of categorial, non-metric input variables, such as a hair colour (for example blonde, brown, black, etc.) and/or ethnic affiliation of a hair type (for example Caucasian, Asian, Afro-American), which may influence a resultant NIR absorption or fluorescence intensity. The input variables in various exemplary embodiments may be detected by employing the hair condition-determining device, for example the hair colour with use of the optical sensor, provided the optical sensor comprises a sensor capable of receiving in a visible spectral range, or possibly a further sensor arranged in the device body, provided the further sensor is capable of receiving in the visible spectral range.

In accordance with various embodiments the plurality of NIR absorption-influencing or fluorescence intensity-influencing parameters may include a hair colour and/or an ethnic affiliation of a hair type. If no sensors for detecting the NIR absorption-influencing or fluorescence intensity-influencing parameters are present in the hair condition-determining device, these parameters may also be provided by employing the input device in the hair condition-determining device.

In accordance with various embodiments the predictive analytics can utilise at least one method from a group of methods, wherein the group of methods includes:
  linear or multi-linear regression, polynomial regression, neural network methods, support vector machine methods, decision tree methods (decision trees, random forest, tree ensembles), and further methods.

In various exemplary embodiments the hair condition-determining device can comprise, as a further sensor, a sensor for determining the external hair damage, for example a sensor for detecting acoustic emissions, for example a microphone, for example a contact microphone.

The sensor for detecting acoustic emissions may also be referred to herein as a microphone for the sake of simplicity. Unless stated otherwise and suitable for the described function, the sensor for detecting acoustic emissions may also be an acceleration sensor for example (which may be suitable for detecting accelerations as a result of acoustic emissions in a certain frequency range) or the like.

The hair condition-determining device in various exemplary embodiments may have one or more measurement systems for acoustic emissions (i.e. noise emissions; a contact microphone from the company Korg can be used as an exemplary measurement system for acoustic emissions) and/or measurement probes for acoustic emissions mounted externally on the device body and/or integrated therein.

In various exemplary embodiments, signals of generated noise or vibration created as hair of the user is combed through can be recorded by employing the sensor device, which comprises the microphone.

The hair condition-determining device in various exemplary embodiments may also have an internal or external amplifier for amplifying signals measured by employing the measurement system for acoustic emissions.

In various exemplary embodiments an analysis of hair damage can be provided by digitalising and evaluating information from the microphone by employing the electronic circuit device.

The information can be provided after a processing or can be provided for a comparison with previously recorded examples (reference data). A degree of hair damage may be known for the reference data, such that for example the degree of hair damage of the most similar reference data can be provided, for example transmitted back, as the result of the comparison in digital form.

In various exemplary embodiments the reference data can be provided and/or the comparison with the reference data can be carried out in, or by employing a cloud server architecture ("cloud" for short).

By employing the use of various further sensors, such as lenses, gyroscopes and accelerometers, it may be possible to determine the position of the hair condition-determining device. For example, gyroscopes and/or accelerometers may be used to determine the start and/or end of a combing/brushing process. On the assumption that a combing/brushing process starts typically at the hair root and ends at the hair tip, a spatially resolved determination of the hair condition information, for example hair root/middle region/tip, can be made possible, optionally in combination with a speed at which the hair condition-determining device is moved, determined by employing the sensors.

Data can be transmitted from the hair condition-determining device to the external data processing device in various exemplary embodiments by employing cables or via known wireless data transmission standards (for example Bluetooth, WLAN, ZigBee, Thread, NFC, etc.).

The present disclosure relates to various embodiments of a hair condition-determining device for providing information regarding a hair condition of hair of a user. The hair condition-determining device can have a device body having at least one first region and one second region, wherein the first region and the second region are designed in such a way that the hair of the user can be moved between the first region and the second region, at least one optional light source arranged in or on the device body for illuminating the hair of the user, at least one optical sensor arranged in or on the device body for sensing light that has been emitted by the light source and has interacted with the hair and/or ambient light that has interacted with the hair, and an electronic circuit device arranged in or on the device body, wherein the electronic circuit device is coupled to the optical sensor in order to receive the detected light, and wherein the electronic circuit device is designed to provide information regarding the hair condition of the user to the user on the basis of the received detected light.

In various exemplary embodiments the hair cam be arranged between the first and the second region during the detection of the light.

In various exemplary embodiments the hair can be moved between the first and the second region during the detection of the light. In various exemplary embodiments the device body can be formed as a comb or as a brush, wherein the first region and the second region may comprise two adjacent comb teeth or two adjacent bristles of the brush.

In various exemplary embodiments the comb or the brush may have a handle, wherein the at least one optical sensor and a light entry region for feeding the light to the optical sensor may be arranged in the handle.

In various exemplary embodiments the light source may comprise a UV light source, and the at least one optical sensor may comprise a detector for visible light for detecting fluorescent light.

In various exemplary embodiments the light source may comprise an NIR light source, and the at least one optical sensor may comprise an NIR detector for detecting near-infrared light.

In various exemplary embodiments the light source may comprise a VIS/NIR light source, and the at least one optical sensor may comprise a VIS/NIR detector for detecting visible light and near-infrared light.

In various exemplary embodiments the electronic circuit device may be designed to determine a recommendation on the basis of the determined hair condition and to provide this recommendation to the user.

In various exemplary embodiments the recommendation may comprise at least one of a haircare product recommendation, a hair-colouring product recommendation, a hairstyling product recommendation, and a hair treatment recommendation.

In various exemplary embodiments the hair condition-determining device may also comprise at least one further sensor for detecting a further hair condition.

In various exemplary embodiments the at least one further sensor may comprise a microphone for determining the surface roughness of the hair.

In various exemplary embodiments the electronic circuit device may comprise a wireless data exchange device.

In various exemplary embodiments a hair condition-determining system is provided. The hair condition-determining system may comprise a hair condition-determining device according to various exemplary embodiments and a display device, wherein the at least one hair condition-determining device may be designed to transmit the hair condition information to the display device by employing the data exchange device.

In various exemplary embodiments the display device may comprise a computer screen, a smartphone, a tablet, an iPad, a smart mirror, or a laptop.

In various exemplary embodiments a method for providing information regarding the condition of the hair of a user is provided. The method may include arranging a hair condition-determining device according to various exemplary embodiments in such a way that the hair of the user faces a light entry region of the hair condition-determining device during an optional illumination of the hair by employing the light source, detecting at least a part of the light which has interacted with the hair and/or detecting ambient light which has interacted with the hair, during the illumination as applicable, and providing information regarding the condition of the hair of the user to the user on the basis of the detected light.

In various exemplary embodiments the light entry region can be designed to feed the light to the at least one optical sensor.

In various exemplary embodiments the method may also comprise a determination of at least one recommendation on the basis of the determined hair condition.

In various exemplary embodiments the recommendation may comprise at least one of a haircare product recommendation, a hair-colouring product recommendation, a hairstyling product recommendation, and a hair treatment recommendation.

In accordance with a further embodiment the hair condition-determining device is designed, after outputting a recommendation, in particular a product recommendation, to receive an input by a user and, on the basis of this input, to initiate an action in relation to the displayed/output product.

For example, the action may relate to the fact that user may be given the opportunity to purchase a product, for example a haircare product, a hair-colouring product and/or a hairstyling product, and the user may arrange for the purchase by making an input. Besides the actual purchase of products, the user may also be provided with more detailed information relating to the purchase. This more detailed information may relate to more detailed treatment and use instructions. The hair condition-determining device for example receives the request that the user wishes to purchase the product, stores the request and/or transmits the request to a company that sells the product. The user is asked by the hair condition-determining device, for example via the output device, to provide his/her personal data (address, bank information, shipping preference, etc.) via the input unit.

Alternatively, the user can be output information detailing where, in the vicinity, the output, for example displayed, product can be purchased locally, for example in a drug store, in a hair salon, in a pharmacy, etc.

Customers are increasingly looking for products tailored to their individual needs. Accordingly, a product produced individually for the user might be recommended, and an ordering process can be initiated, for example by loading a website of a manufacturer of tailored hair treatment products.

Such a product may be a hair treatment product produced especially for the particular user or may be what is known as a "mass customised" product. In the case of a "mass customised" product, customisation can be achieved by varying just a few features of a product, however they are considered to be decisive features by the customer. These "mass customised" products are preferably based on the concept of modularisation, that is to say the product can be composed individually from various modules/components.

There are often numerous dependencies between the many different features/ingredients of a product, and these can be expressed as "dos" and "don'ts". In order to obtain a clear product definition it may be advantageous for the ordering process to be performed with the aid of a product configurator. This configurator assists the user in choosing the features/ingredients and advises him/her of the admissible/inadmissible combinations of features, wherein the latter then cannot be selected.

In the case of hair treatment products the relevant product features comprise in particular the chemical ingredients of the products, the physical properties of the products, and the formulation of the products. With the aid of a product configurator, for example the choice of chemically and/or physically incompatible ingredients or the choice of ingredients unsuitable for the determined hair condition can be avoided. Conversely, the choice of ingredients suitable for the determined hair condition can be specified or proposed by the product configurator.

It is also possible to produce an individual hair treatment product on-site, that is to say for example in a hair salon or at a point of sale for hair treatment products, for example in a drug store, by employing a mixing device, preferably an intelligent mixing device (smart mixer).

In various exemplary embodiments the determined hair condition may comprise at least one of hair damage and hair status.

The hair damage may be oxidative hair damage in various exemplary embodiments.

The hair status in various exemplary embodiments may comprise a hair colour, a water content of hair and/or a hair thickness.

In accordance with a further aspect a method for determining a treatment agent on the basis of the determined hair condition is described. This method has the following steps: consulting the determined hair condition and selecting a treatment product for hair on the basis of the determined hair condition and outputting information regarding the selected treatment product.

In accordance with a further aspect a computer program product which is configured to carry out the method as described herein when run on a device as also described herein is described.

In the present description the terms "predictive analytics", "big data" and "data mining" are used synonymously.

Where reference is made herein to a smartphone, this shall be understood to be representative for all similar types of portable data processing device, i.e. smartphones, tablets, iPads, laptops, etc., unless otherwise evident from the context. The same is true for smartphone cameras and the like.

A comb is understood herein to mean a device for combing hair, in which comb teeth are formed in a substantially one-dimensional arrangement.

A brush is understood herein to mean a device for brushing hair, in which bristles are formed in a substantially two-dimensional arrangement.

A hair dye is understood herein to mean an agent for changing hair colour. The hair dye may thus be either a colourant for producing a hair colour (for example black, brown or red), or a bleaching agent for removing/lightening a hair colour be destroying melanin.

Figure 2A:
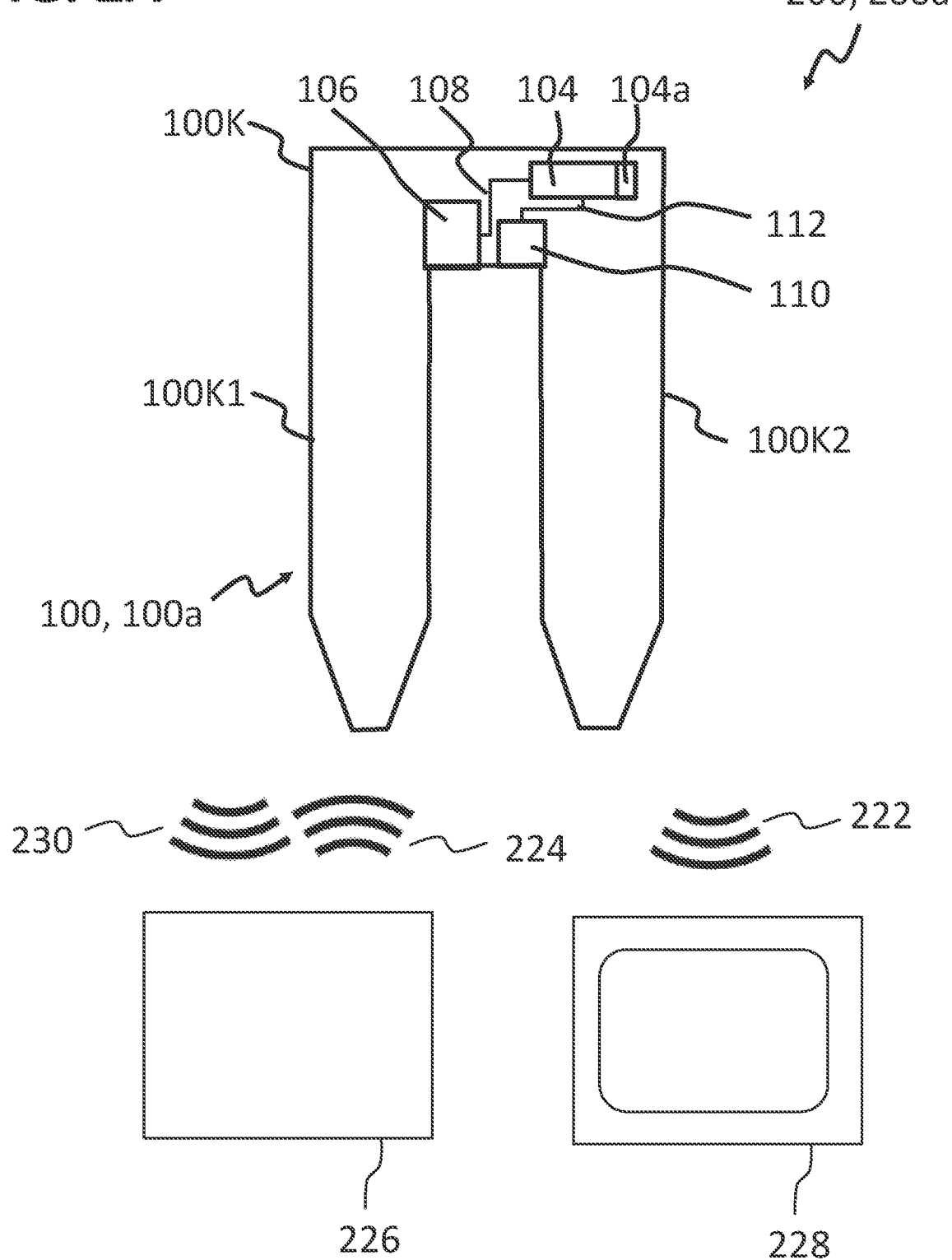
FIGS. 2A, 2B, 2C and 2D each show a schematic depiction of a hair condition-determining device according to various exemplary embodiments.
Figure 2B:
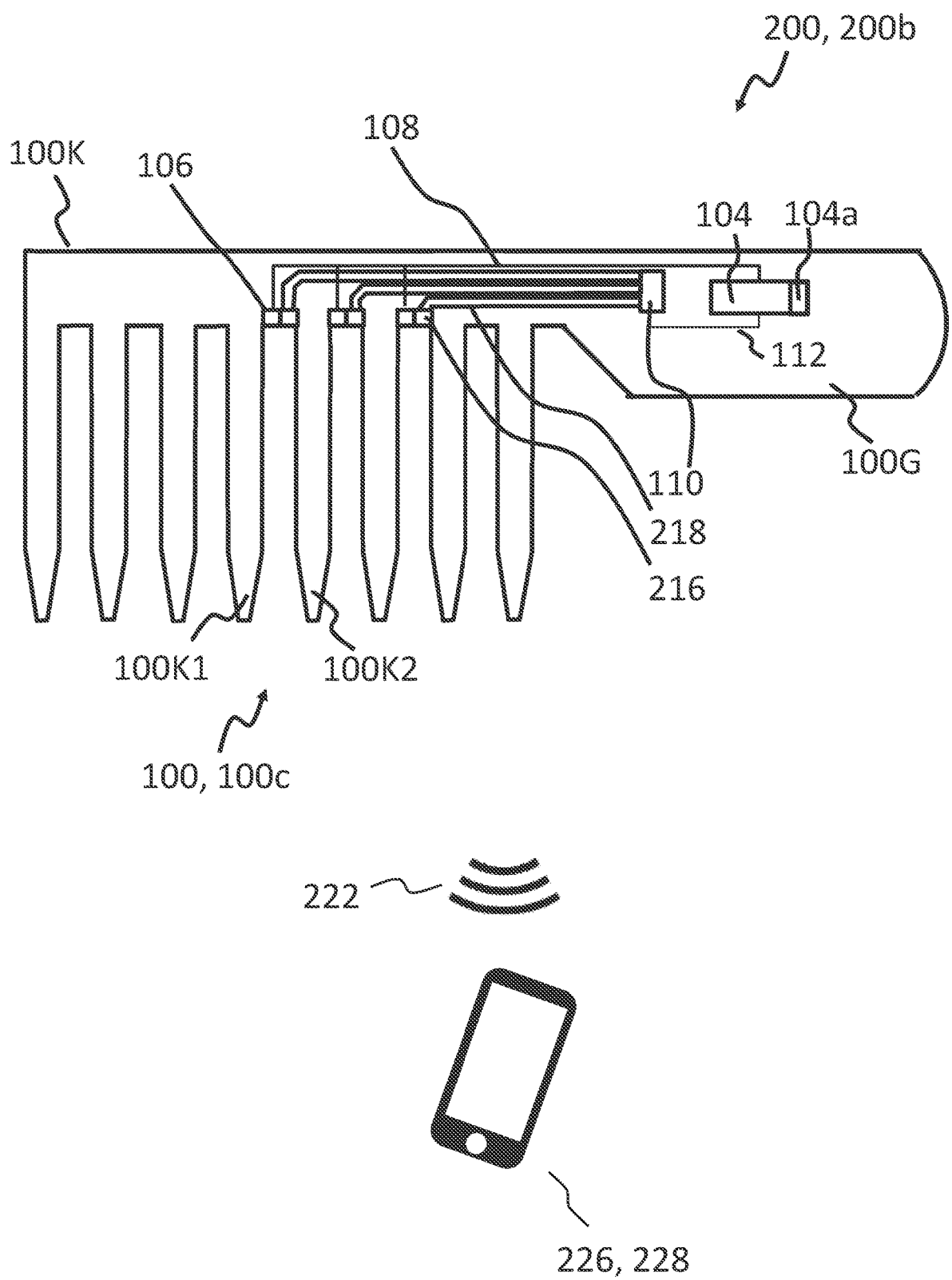
Figure 2C:
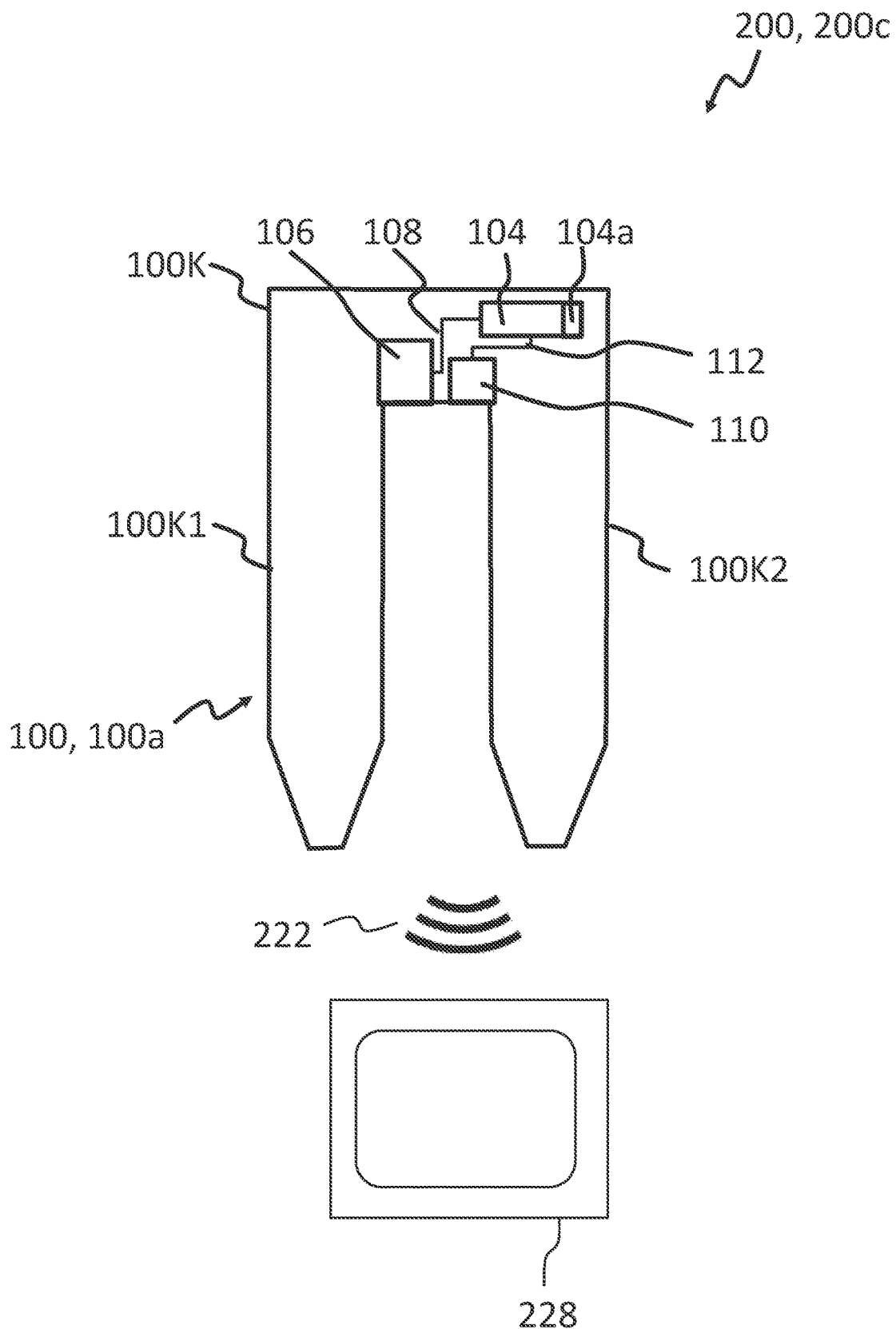
Figure 2D:
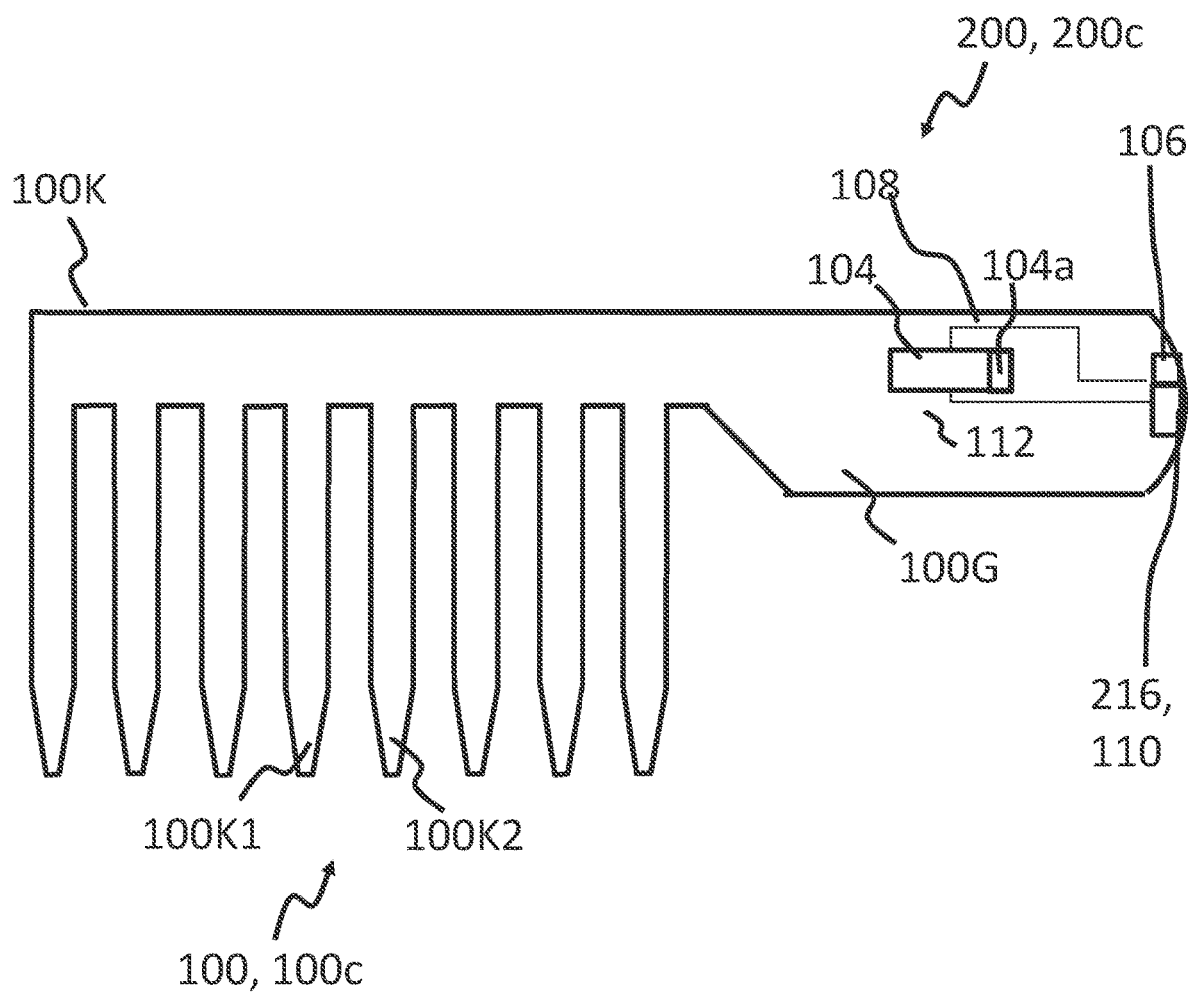
Figure 3A:
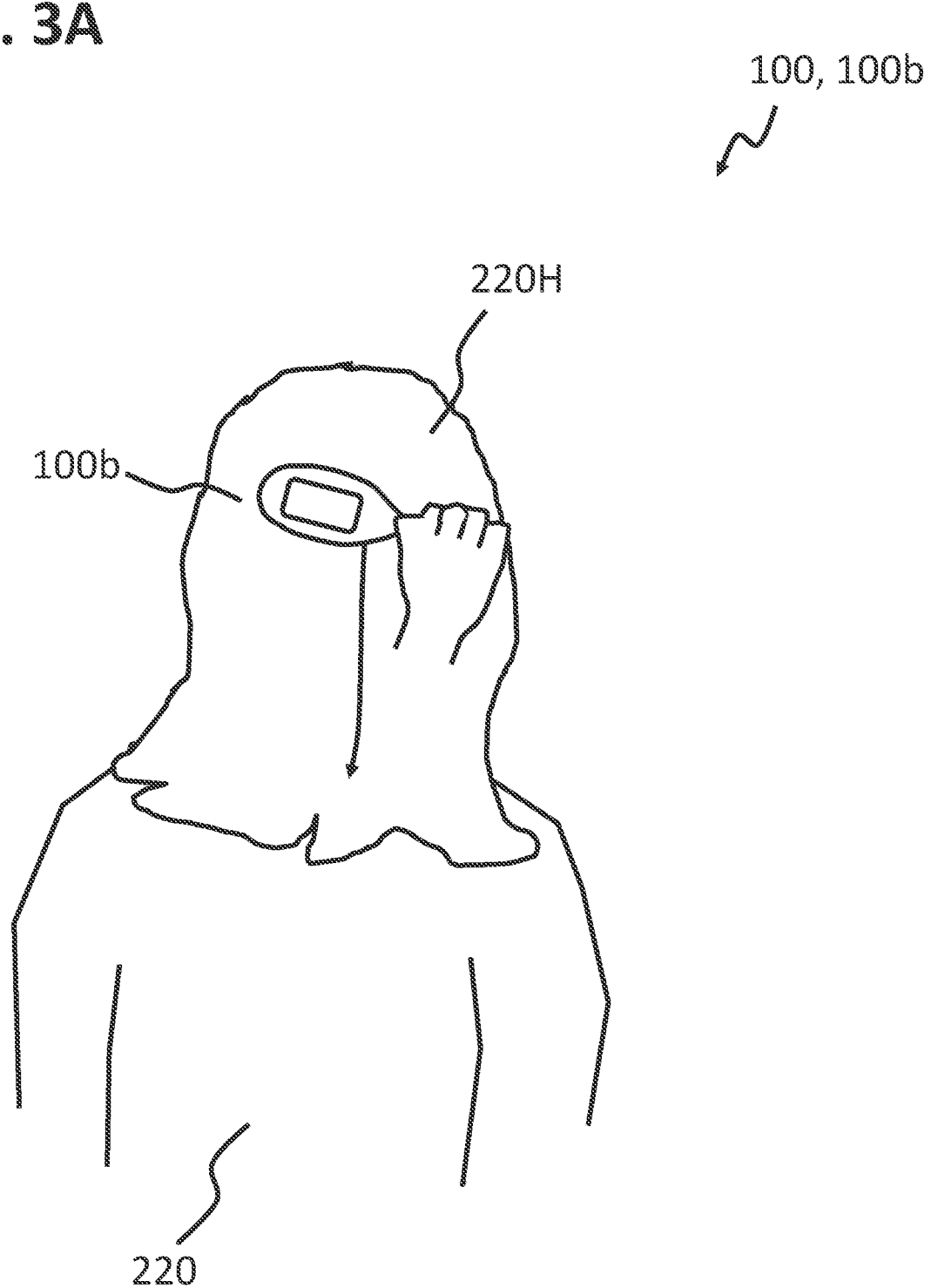
FIG. 3A shows a schematic illustration of use of a hair condition-determining device according to various exemplary embodiments.
Figure 3B:
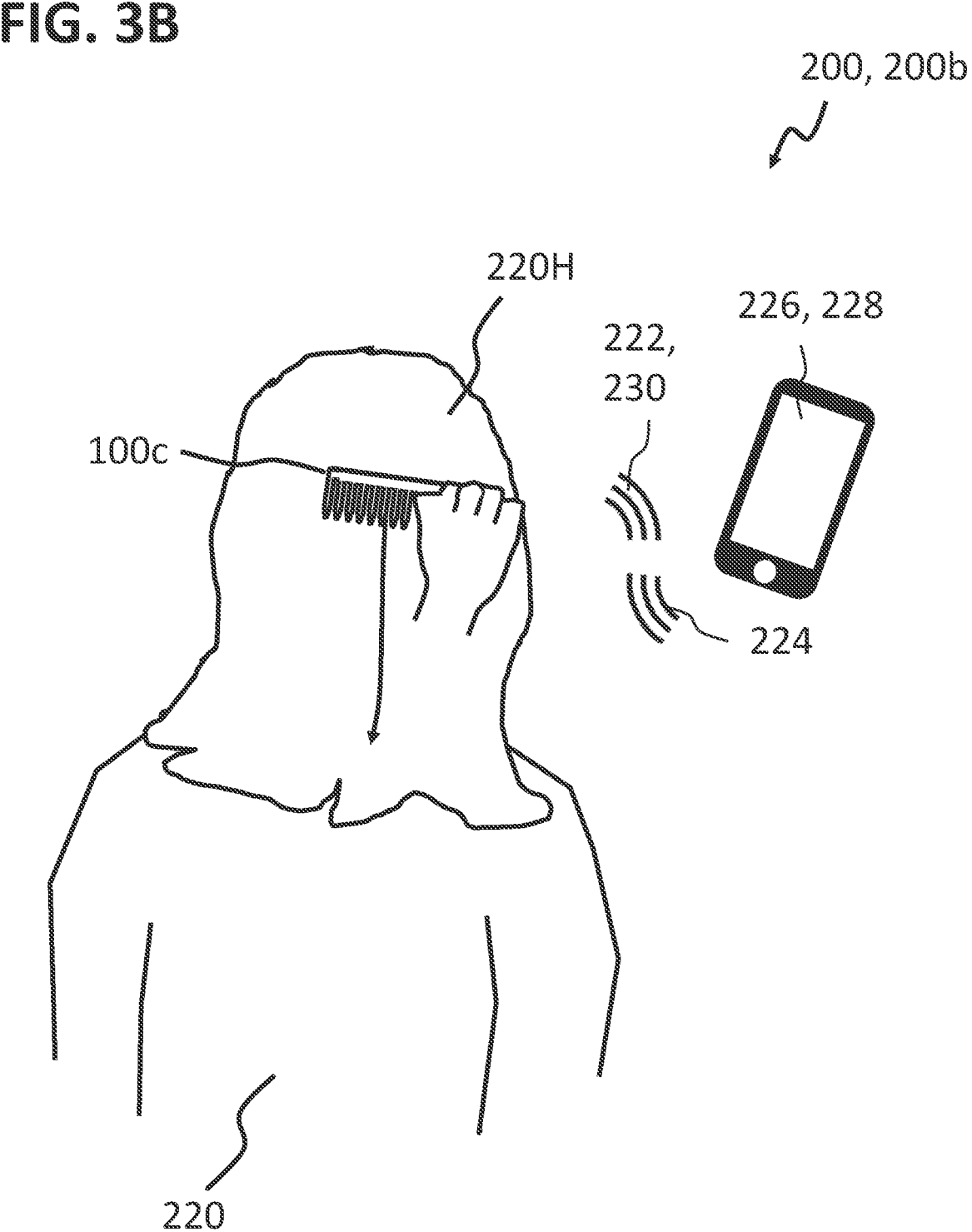
FIG. 3B shows a schematic illustration of use of a hair condition-determining device according to various exemplary embodiments.

FIG. 1A and FIG. 1B each show a schematic depiction of a hair condition-determining device 100 according to various exemplary embodiments, FIG. 2A, FIG. 2B, FIG. 2C and FIG. 2D each show a schematic depiction of a hair condition-determining device 200 according to various exemplary embodiments, FIG. 3A shows a schematic illustration of use of a hair condition-determining device according to various exemplary embodiments, and FIG. 3B shows a schematic illustration of use of a hair condition-determining device according to various exemplary embodiments.

Different exemplary embodiments of the hair condition-determining device 100 and of the hair condition-determining system 200 are denoted by letters after the reference numeral.

In various exemplary embodiments the hair condition-determining device 100 may comprise a device body 100K with at least one first region 100K1 and one second region 100K2, wherein the first region 100K1 and the second region 100K2 are designed such that the hair 220H of the user 220 is movable between the first region 100K1 and the second region 100K2.

In various exemplary embodiments the device 100 may also comprise at least one light source 106 arranged in or on the device body 100K for illuminating hair 220H of the user 220 moved between the first region and the second region.

In various exemplary embodiments the device 100 may also comprise at least one optical sensor 110 arranged in or on the device body 100K for detecting light which has been irradiated by the light source 106 and has interacted with the hair 220H moved between the first region and the second region.

In various exemplary embodiments the device 100 may also comprise an electronic circuit device 104 arranged in or on the device body 100K, wherein the electronic circuit device 104 is suitable for coupling to the optical sensor 110 in order to receive a signal generated by employing the detected light, and wherein the electronic circuit device 104 may be designed to determine and to provide information regarding the condition of the hair of the user 220 on the basis of the received signal.

In various exemplary embodiments the hair condition-determining device 100 may have an optical sensor 110 for determining hair damage and/or the condition of the hair 220H.

In various exemplary embodiments the hair condition-determining device 100 may have an optical sensor 110 for determining the cysteic acid content of the hair 220H.

In various exemplary embodiments the hair condition-determining device 100 may have an optical sensor 110 for determining the water content of the hair 220H.

In various exemplary embodiments the hair condition-determining device 100 may have an optical sensor 110 for determining the colour of the hair 220H.

In various exemplary embodiments the optical sensor 110e for determining the cysteic acid content of the hair 220H, as described above, may comprise a camera and/or a spectrometer for detecting fluorescent light in a wavelength range of visible light, wherein the fluorescent light is emitted by the hair 220H when irradiated with UV light.

In order to irradiate the hair with UV light, the hair condition-determining device 100 may comprise a light source 106, for example a UV lamp, a UV-LED or the like, which is suitable for irradiating UV light in a wavelength range which excites damaged hair to emit fluorescent light.

The fluorescent light may be an inherent fluorescence of the damaged hair 220H, and/or a fluorescence of fluorescence dye adsorbed in the hair 220H. The hair 220H might have been removed from the head, for example in order to wet the hair with a fluorescence dye solution and/or in order to record the fluorescent light, or the hair might remain on the head of the user, for example as the inherent fluorescence of the hair is recorded.

In various exemplary embodiments the irradiation, detection, and an analysis of the detected sensor signal can be performed as described above. A degree of hair damage can thus also be determined as hair condition information.

In various exemplary embodiments the optical sensor 110 for determining the cysteic acid content or another constituent content of the hair 220H may comprise, as described above, a camera and/or a spectrometer for detecting (near-)infrared light, wherein the (near-)infrared light is emitted by the hair 220H whilst the hair 220H is irradiated by the (near-)infrared light and interacts therewith, for example absorbs part of said light.

For irradiation with the (N)IR light the light source 106 may comprise a (N)IR lamp which is suitable for irradiating (N)IR light at least in a wavelength range in which cysteic acid absorbs light.

In order to control the light source 106, the light source 106 may be connected in various exemplary embodiments to the electronic circuit device 104, for example by employing a connection 108.

In various exemplary embodiments the irradiation, detection, and an analysis of the detected sensor signal can be performed as described above. A degree of hair damage and/or a hair status can thus be determined as hair condition information.

An exit region of the light source 106 from the device body and an entry region of the optical sensor 110, in various exemplary embodiments, can be arranged relative to one another in such a way that light which is irradiated by the light source 106 toward the hair 220H, after having interacted with the hair 220H, is irradiated at least in part in the direction of the optical sensor 110, such that it can be detected by the optical sensor 110.

The optical sensor 110 formed as a spectrometer may be designed in various exemplary embodiments to detect the fluorescent light or (N)IR light such that said light can be analysed, and also to allow a determination of the hair colour or for example the water content of the hair.

In various exemplary embodiments the optical sensor 110 may be arranged adjacently to the light source 106, as shown by way of example in FIG. 1A, FIG. 2A, FIGS. 2C and 2D for the hair condition-determining device 100a.

In various exemplary embodiments the optical sensor 110 may be arranged inside the light source 106 (for example surrounded by the light source), as shown by way of example in FIG. 1B for the hair condition-determining device 100b (a part of the bristles is not shown in FIG. 1B so as to free the view of the sensor 110 and the light source 106).

In various exemplary embodiments, for example when only little space is available, for example in the combing region of a comb, the light source 106 and/or the optical sensor 110 can be arranged at a distance from the exit or entry region. As described above, in various exemplary embodiments the light source 106 can be arranged at a distance from the light exit region, for example at a point of the device body 100K which has more space available, and the light to be irradiated can be guided to the light exit region by employing a light-guiding device.

In various exemplary embodiments, as shown by way of example in FIG. 2B for the hair condition-determining device 100c, the optical sensor 110 can be arranged at a distance from a light entry region 216, for example at a point of the device body 100K which has more space available, and the light entering the light entry region 216 can be guided to the optical sensor 110 (for example the detector) by employing a light-guiding device 218.

In various exemplary embodiments, as shown in FIG. 2D, the at least one optical sensor 110 (and possibly the light source 106) can be arranged in the handle 100G of the device body 100K, and the light entry region 216 for feeding the light from the hair to the optical sensor 110 can also be arranged in the handle, for example at a handle end. In order to determine the hair condition, the comb or the brush can be arranged such that the light entry region 216 is arranged facing the hair 102H, that is to say in the exemplary embodiment from FIG. 2D for example with the handle end towards the hair 102H. For example it may thus be made possible that a hairdresser rotates the comb or the brush slightly during a hairstyling process and takes a measurement for detecting the hair condition.

In various exemplary embodiments an arrangement of the light entry region 216 at a point of the device body 100K at which the first region 100K1 and the second region 100K2 are mounted on the device body 100K, i.e. between the teeth of the comb or between the bristles of the brush, may make it possible to ensure a substantially constant distance between the light entry region 216 and the hair 220H arranged between the first region 100K1 and the second region 100K2, without having to instruct the user 220 as to how he/she should position the hair condition-determining device 100 relative to his/her hair, because a combing or brushing process is usually performed in such a way that the hair is in contact with the device body 100K between the teeth 100K1, 100K2 or bristles.

The range of variation in the measured values can thus be reduced without additional effort, i.e. hair condition measurement results that are more reliable can be attained.

In various exemplary embodiments a plurality of light sources 106 and/or a plurality of light exit regions can be provided.

In various exemplary embodiments a plurality of optical sensors 110 and/or a plurality of light entry regions 216 can be provided, wherein the plurality of optical sensors 110 may be designed to detect the same kind of signal, for example either fluorescent light or (near-)infrared or visible light. Alternatively, the plurality of optical sensors 110 can be designed to detect different types of signals, for example fluorescence light and (near-)infrared light or visible light and (near-)infrared light or fluorescent light, visible light and (near-)infrared light.

In various exemplary embodiments at least one further optical sensor may also be provided (not shown), which may be designed to detect light so as to detect at least one further sensor value, which can be used when determining the hair condition. The at least one further optical sensor may comprise for example a colour camera and/or a spectrometer, which can be designed to detect light in a number of visible wavelength ranges, which enables the hair colour of the user 220 to be determined, for example as described above.

In various exemplary embodiments the hair condition-determining device may comprise an output device 128, which can be designed to provide the determined hair condition and optionally a recommendation determined by employing the determined hair condition.

The output device 128, in various exemplary embodiments, can be a display device 128 (also referred to as a display), as shown by way of example in FIG. 1B. Alternatively or additionally the hair condition-determining device may comprise another output device 128, for example a loudspeaker.

The determined hair condition (for example the determined degree of hair damage) and optionally a recommendation determined by employing the determined hair condition, for example a recommendation for a hair-colouring product, a haircare product, hairstyling and/or a hair treatment, can be provided by employing the output device 128.

In various exemplary embodiments an external output device 228 can be provided and, together with the hair condition-determining device 100, can form a hair condition-determining system 200 as shown by way of example in FIG. 2A, 2B, 2C, 2D and FIG. 3B.

The electronic circuit device 104 can transmit the data that is to be displayed to the output device 228 in the form of a signal 222, for example by employing the device 104a for wireless data transfer.

The output device 228, for example a display 228, in various exemplary embodiments, as shown in FIG. 2A and FIG. 2C, may perform merely an output function.

In various exemplary embodiments, as shown for example in FIG. 2B and in FIG. 3B, the output device 228 may be part of the external data processing device 226. In this case the external data processing device 226 may optionally perform additional tasks in addition to an output function, for example may be used as the input device, to determine the hair condition and/or the recommendation, to store results for creating a progression profile over time, etc.

In various exemplary embodiments the hair condition-determining device may comprise an input device. The input device is only shown in the drawings for examples in which the display 128 integrated into the device 100 or an external display 228 can also be used as an input device, for example in the case of a touch-sensitive display. For example the input device can be used in order to input a desired result, for example a desired hair colour, a desired state of nourishment, a desired styling (for example curly with graduated curliness, or the like). Furthermore, the input device can be used in order to provide the hair condition-determining device with further information which can be taken into consideration optionally when determining the recommendation, for example whether a product should possibly be waterproof, should contain a UV filter, age, ethnicity and/or gender of the user, etc.

In various exemplary embodiments the at least one further sensor may comprise a microphone for determining the surface roughness of the hair, for example as described above.

In various exemplary embodiments the degree of (surface) damage of the hair can be determined on the basis of the determined surface roughness, as described above.

In various exemplary embodiments the recorded light and/or the recorded noise or optionally another or further detected sensor value can be transferred to the electronic circuit device 104 as raw data and/or in processed form, for example as a digital photo or another quantification of the recorded light, as an audio file, Fourier transformation or the like, for example by employing a connection 112.

In various exemplary embodiments the electronic circuit device 104 can be designed to determine the hair condition, for example the degree of hair damage and/or the hair status, and/or the recommendation directly, i.e. itself, for example by employing a software, for example as described above.

In various exemplary embodiments the electronic circuit device 104 can be designed to determine the hair condition, for example the degree of hair damage and/or the hair status, and/or the recommendation indirectly, for example by employing a transmission of the sensor raw data and/or of partially analysed sensor data and/or of a hair status to an external data processing device 226, for example to a portable data processing device (for example a smartphone or the like), as shown by way of example in FIG. 2B and FIG. 3B, or for example to another external data processing device, for example a cloud server architecture 226 ("cloud"), as shown by way of example in FIG. 2A, wherein, when providing information to the cloud the electronic circuit device 104 may also be designed to receive a result from the external data processing device (for example the cloud) 226 and to provide it by employing an output device 128, 228.

In various exemplary embodiments the electronic circuit 104 may comprise a device 104a for wireless data transfer, for example for data transfer by employing WLAN, Bluetooth, ZigBee, Thread, NFC or the like, for example as described above. Data can be transferred to or received by the external data processing device 226 by employing the device 104a for wireless data transfer.

In various exemplary embodiments the hair condition-determining device can be formed as a learning system, for example in that the user 220 and/or further users provides/provide the hair condition prior to implementation of the recommendation and the hair condition after implementation of the recommendation to the data processing device (for example by employing the cloud).

In various exemplary embodiments the determination of the hair condition can comprise a computer-aided determination of the degree of hair damage and/or the hair colour or another hair status, for example a water content of the hair, for example by employing predictive analytics, for example as described above.

In various exemplary embodiments the determination of a recommendation may comprise a computer-aided determination of a hair treatment agent and/or a hair treatment recommendation, for example by employing predictive analytics, with inclusion of the determined hair condition, for example as described above.

In the case of indirect determination, the external data processing device 226, for example the smartphone, may be equipped for example with an appropriate software, for example an app, for example as described above.

In various exemplary embodiments a cysteic acid content can be determined by employing the electronic circuit device 104 or by employing the external data processing device 226 on the basis of a measure (for example an equivalent width) for the (N)IR absorption or the determined fluorescence intensity. To this end, for example as described above, mathematical models from the field of predictive analytics can be used in order to determine a relationship between the measure for the (N)IR absorption or the (standardised) fluorescence intensity and an associated cysteic acid content (and thus a degree of damage of the hair).

In various exemplary embodiments a relationship for example between cysteic acid content and (N)IR absorption or cysteic acid content and fluorescence intensity or corresponding data values, for example in the form of associated data pairs, can be included as independent parameters in the model, said parameters having been determined or mathematically modelled by measurement of standard hair samples having a cysteic acid content determined on the basis of known complex methods.

Accordingly, other sensor values can be used in various exemplary embodiments.

In various exemplary embodiments the degree of damage of the hair can be determined in a categorial scale (for example slight, medium, severe).

In various exemplary embodiments the degree of damage can be determined in a metric scale (for example percentage of the content of cysteic acid, loudness of combing noise in dB, or the like).

In various exemplary embodiments, instead of the method based on predictive analytics, other, for example simpler, methods can be used to determine the hair condition, for example the degree of damage or the hair colour, and/or to determine the recommendation.

In various exemplary embodiments, in order to provide the hair condition after the treatment, a determination of the hair condition after the treatment with the hair treatment agent can be used by employing the hair condition determination device. In other exemplary embodiments another, for example structurally identical, device can be used in order to determine the hair condition after the treatment, and the determined hair condition can be transmitted to the data processing device.

FIG. 4 shows a flow chart 400 showing a method for providing a hair treatment agent in accordance with various exemplary embodiments. In order to carry out the method, a device according to various exemplary embodiments as described above can be used.

The method can comprise moving a hair condition-determining device in such a way that the hair of the user moves between the first region and the second region (in 410), the hair is illuminated by employing the light source (in 420), during the illumination at least a part of the light which has interacted with the hair is detected (in 430), hair condition information regarding the hair of the user is determined on the basis of the detected light (in 440), and the hair condition information is provided (in 450).

Further advantageous embodiments of the method will become clear from the description of the device, and vice versa.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A hair condition-determining device for providing information regarding a hair condition of hair of a user, the device having:
    a device body having at least one first region and one second region configured such that the hair of the user can be moved between the first region and the second region;
    at least one optional light source, arranged in or on the device body, for illuminating the hair of the user;
    at least one optical sensor, arranged in or on the device body, for detecting light which has been irradiated by the light source and has interacted with the hair, and/or ambient light which has interacted with the hair; and
    electronic circuit device arranged in or on the device body,
    wherein the electronic circuit device is coupled to the optical sensor in order to receive a signal generated by employing the detected light, and
    wherein:
        the electronic circuit device is designed to determine information regarding the hair condition of the user on the basis of the received signal and to provide the information to the user,
        the at least one optical sensor is configured to take one or more recordings in a fluorescence range and/or in a near-infrared range (NIR range),
        the electronic circuit is configured, on the basis of the received signal, to determine a degree of hair damage by determining a cysteic acid content, and
        the electronic circuit is configured, on the basis of the received signal, to determine a water content of the hair.

2. The hair condition-determining device according to claim 1,
    wherein the device body is formed as a comb or as a brush, and wherein the first region and the second region comprise two adjacent comb teeth or two adjacent brittles.

3. The hair condition-determining device according to claim 2, wherein the light source comprises a UV light source, and the at least one optical sensor comprises a detector for detecting fluorescent light.

4. The hair condition-determining device according to claim 2, wherein the light source comprises an NIR light source, and the at least one optical sensor comprises an NIR detector for detecting near-infrared light.

5. The hair condition-determining device according to claim 2, wherein the electronic circuit device is designed to determine a recommendation on the basis of the determined hair condition and to provide this recommendation to the user.

6. The hair condition-determining device according to claim 1,
    wherein the light source comprises a UV light source, and the at least one optical sensor comprises a detector for detecting fluorescent light.

7. The hair condition-determining device according to claim 6, wherein the light source comprises an NIR light source, and the at least one optical sensor comprises an NIR detector for detecting near-infrared light.

8. The hair condition-determining device according to claim 6, wherein the electronic circuit device is designed to determine a recommendation on the basis of the determined hair condition and to provide this recommendation to the user.

9. The hair condition-determining device according to claim 1,
    wherein the light source comprises an NIR light source, and the at least one optical sensor comprises an NIR detector for detecting near-infrared light.

10. The hair condition-determining device according to claim 1,
    wherein the electronic circuit device is designed to determine a recommendation on the basis of the determined hair condition and to provide this recommendation to the user.

11. The hair condition-determining device according to claim 10, wherein the recommendation comprises at least one of a haircare product recommendation, a hairstyling product recommendation, hair-colouring product, and a hair treatment recommendation.

12. The hair condition-determining device according to claim 1, further having:
    at least one further sensor for detecting a further hair condition.

13. The hair condition-determining device according to claim 12,
    wherein the at least one further sensor has a microphone.

14. The hair condition-determining device according to claim 1,
    wherein the electronic circuit device comprises a wireless data exchange device.

* * * * *